US010549128B2

(12) United States Patent
Phillips et al.

(10) Patent No.: US 10,549,128 B2
(45) Date of Patent: Feb. 4, 2020

(54) SYSTEMS AND METHODS FOR IMAGING AND ABLATING TISSUE

(71) Applicant: VytronUS, Inc., Sunnyvale, CA (US)

(72) Inventors: Patrick Phillips, Los Altos, CA (US); Danielo B. Piazza, Livermore, CA (US)

(73) Assignee: VytronUS, Inc., Sunnyvale, CA (US)

( * ) Notice: Subject to any disclaimer, the term of this patent is extended or adjusted under 35 U.S.C. 154(b) by 456 days.

(21) Appl. No.: 15/343,128

(22) Filed: Nov. 3, 2016

(65) Prior Publication Data

US 2017/0120080 A1    May 4, 2017

Related U.S. Application Data

(60) Provisional application No. 62/250,676, filed on Nov. 4, 2015.

(51) Int. Cl.
*A61B 18/12* (2006.01)
*A61N 7/02* (2006.01)
(Continued)

(52) U.S. Cl.
CPC ............. *A61N 7/022* (2013.01); *A61B 8/445* (2013.01); *A61B 8/5253* (2013.01); *A61B 34/10* (2016.02);
(Continued)

(58) Field of Classification Search
CPC ................ A61B 18/00; A61B 18/1492; A61B 2018/00357; A61B 2018/00363;
(Continued)

(56) References Cited

U.S. PATENT DOCUMENTS

| 4,641,649 A | 2/1987 | Walinsky et al. |
| 5,246,438 A | 9/1993 | Langberg |
| (Continued) |

FOREIGN PATENT DOCUMENTS

WO      9902096      1/1999

OTHER PUBLICATIONS

Office Action dated Nov. 22, 2017 for U.S. Appl. No. 15/669,675.
(Continued)

*Primary Examiner* — Michael F Peffley
*Assistant Examiner* — Amanda L Zink
(74) *Attorney, Agent, or Firm* — MLO, a professional corp.

(57) ABSTRACT

Systems and methods for a graphical user interface for an ablation procedure include a display, a controller in electronic communication with the display, a catheter coupled to the controller, and a graphical user interface generated by the controller and shown on the display. The catheter has a distal tip comprising an ultrasound transducer. The ultrasound transducer is configured to emit an ultrasound beam. The graphical user interface includes a three-dimensional anatomical reference map of a chamber of body tissue to be ablated, where a lesion path is superimposed on the anatomical reference map; a catheter position relative to the chamber; and a window showing data. The data includes at least one of a) a distance between the ultrasound transducer and a surface of the body tissue, b) a dosing plan, c) a tissue thickness, and d) a tissue property.

22 Claims, 12 Drawing Sheets

(51) Int. Cl.
| | |
|---|---|
| *A61B 34/10* | (2016.01) |
| *A61B 34/20* | (2016.01) |
| *A61B 34/00* | (2016.01) |
| *A61B 8/00* | (2006.01) |
| *A61B 8/08* | (2006.01) |
| A61B 18/00 | (2006.01) |
| A61N 7/00 | (2006.01) |

(52) U.S. Cl.
CPC .............. *A61B 34/20* (2016.02); *A61B 34/25* (2016.02); *A61B 8/466* (2013.01); *A61B 2018/00357* (2013.01); *A61B 2018/00363* (2013.01); *A61B 2018/00577* (2013.01); *A61B 2018/00642* (2013.01); *A61B 2034/105* (2016.02); *A61B 2034/107* (2016.02); *A61B 2034/2051* (2016.02); *A61B 2034/258* (2016.02); *A61N 2007/0052* (2013.01)

(58) Field of Classification Search
CPC .......... A61B 2018/00577; A61B 2018/00642; A61B 2034/105; A61B 2034/107; A61B 2034/2051; A61B 2034/2074; A61B 2034/258; A61B 2505/05; A61B 2576/023; A61B 34/10; A61B 34/20; A61B 34/25; A61B 5/0033; A61B 5/0064; A61B 5/02125; A61B 8/12; A61B 8/44; A61B 8/466; A61B 8/5253; A61N 8/44; A61B 8/466; A61B 8/5253; A61N 2007/0052; A61N 7/022

See application file for complete search history.

(56) References Cited

U.S. PATENT DOCUMENTS

| | | | |
|---|---|---|---|
| 5,295,484 A | 3/1994 | Marcus et al. | |
| 5,314,466 A | 5/1994 | Stern et al. | |
| 5,365,562 A * | 11/1994 | Toker ..................... | G03B 42/02 250/367 |
| 5,405,346 A | 4/1995 | Grundy et al. | |
| 6,012,457 A | 1/2000 | Lesh | |
| 6,024,740 A | 2/2000 | Lesh et al. | |
| 6,052,576 A | 4/2000 | Lambourg | |
| 6,064,902 A | 5/2000 | Haissaguerre et al. | |
| 6,117,101 A | 9/2000 | Diederich et al. | |
| 6,161,543 A | 12/2000 | Cox et al. | |
| 6,164,283 A | 12/2000 | Lesh | |
| 6,245,064 B1 | 6/2001 | Lesh et al. | |
| 6,254,599 B1 | 7/2001 | Lesh et al. | |
| 6,305,378 B1 | 10/2001 | Lesh | |
| 6,383,151 B1 | 5/2002 | Diederich et al. | |
| 6,416,511 B1 | 7/2002 | Lesh et al. | |
| 6,502,576 B1 | 1/2003 | Lesh | |
| 6,514,249 B1 | 2/2003 | Maguire et al. | |
| 6,547,788 B1 | 4/2003 | Maguire et al. | |
| 6,605,084 B2 | 8/2003 | Acker et al. | |
| 6,635,054 B2 | 10/2003 | Fjield et al. | |
| 6,652,515 B1 | 11/2003 | Maguire et al. | |
| 6,666,858 B2 | 12/2003 | Lafontaine | |
| 6,780,183 B2 | 8/2004 | Jimenez et al. | |
| 6,814,733 B2 | 11/2004 | Schwartz et al. | |
| 6,872,205 B2 | 3/2005 | Lesh et al. | |
| 6,929,639 B2 | 8/2005 | Lafontaine | |
| 6,949,097 B2 | 9/2005 | Stewart et al. | |
| 6,953,460 B2 | 10/2005 | Maguire et al. | |
| 6,954,977 B2 | 10/2005 | Maguire et al. | |
| 6,955,173 B2 | 10/2005 | Lesh | |
| 6,964,660 B2 | 11/2005 | Maguire et al. | |
| 6,966,908 B2 | 11/2005 | Maguire et al. | |
| 6,996,908 B2 | 2/2006 | Orloff et al. | |
| 6,997,925 B2 | 2/2006 | Maguire et al. | |
| 7,306,593 B2 | 12/2007 | Keidar et al. | |
| 8,221,402 B2 * | 7/2012 | Francischelli ........... | A61N 7/02 606/27 |
| 8,224,422 B2 | 7/2012 | Mottola | |
| 8,600,477 B2 * | 12/2013 | Beyar ..................... | A61B 6/12 128/899 |
| 2005/0267453 A1 | 12/2005 | Wong et al. | |
| 2007/0265610 A1 | 11/2007 | Thapliyal et al. | |
| 2008/0039746 A1 * | 2/2008 | Hissong ................. | A61N 7/022 601/3 |
| 2010/0274239 A1 * | 10/2010 | Paul .................... | A61B 18/1206 606/33 |
| 2011/0144524 A1 * | 6/2011 | Fish .................... | A61B 18/1492 600/547 |
| 2012/0059249 A1 * | 3/2012 | Verard ............... | A61B 1/00071 600/424 |
| 2012/0277763 A1 | 11/2012 | Greenblatt et al. | |
| 2014/0277032 A1 * | 9/2014 | Ahn ........................ | A61N 7/02 606/169 |

OTHER PUBLICATIONS

Burak et al., Radiofrequency ablation of invasive breast carcinoma followed by delayed surgical excision, Cancer 98.7, Jun. 2003, 1369-1376.

Cox et al. "Current status of the Maze procedure for the treatment of atrial fibrillation," Semin Thorac Cardiovasc Surg. Jan. 2000;12(1):15-19.

Cox et al., "Electrophysiologic basis, surgical development, and clinical results of the maze procedure for arial flutter and atrial fibrillation," Adv Card Surg. 1995;6:1-67.

Cox et al., "Modification of the maze procedure for atrial flutter and atrial fibrillation, II, Surgical technique of the maze III procedure," J Thorac Cardiovasc Surg. Aug. 1995;110(2):485-95.

Cox et al., "The development of the Maze procedure for the treatment of atrial fibrillation," Semin Thorac Cardiovasc Sug. Jan. 2000;12(1):2-14.

Danik et al, Evaluation of catheter ablation of periatrial ganglionic plexi in patients with atrial fibrillation, Am J Cardiol, Apr. 2008, 102:578-83.

Gazelle et al, Tumor ablation with radio-frequency energy, Radiology, Dec. 2000, 217:6333-6346.

Gentry et al., "Integrated Catheter for 3-D Intracardiac Echocardiography and Ultrasound Ablation," IEEE Transactions on Ultrasonics, Ferroelectrics, and Frequency Control, Jul. 2004, vol. 51, No. 7, pp. 799-807.

Gillinov et al., "Atrial fibrillation: current surgical options and their assessment," Annals ofThoracic Surgery 2002; 74:2210-7; retrieved from the Internet on Aug. 19, 2009: http://ats.ctsnetjournals.org/cgi/reprint/74/6/2210.

Goldberg et al, Image-guided radiofrequency tumor ablation: challenges and opportunities, I. J Vase Interv Radiol, Sep. 2001, 12:1020-1032.

Goldberg et al, Thermal ablation therapy for focal malignancy: a unified approach to underlying principles, techniques, and diagnostic imaging guidance. AJR Am J Roentgenol Feb. 2000; 174:323-331.

Goldberg et al., Percutaneous Tumor Ablation: Increased Coagulation by Combining Radio-frequency Ablation and Ethanol Instillation in a Rat Breast Tumor Model 1, Radiology 217.3, Dec. 2000, 827-831.

Haissaguerre et al., "Spontaneous Initiation of Atrial Fibrillation by Ectopic Beats Originating in the Pulmonary Veins," New England J Med., Sep. 3, 1998; 339(10):659-666; retrieved from the Internet on Aug. 19, 2009: http://content.nejm.org/cgi/reprint/339/10/659.pdf.

International Search Report and Written Opinion dated Jan. 23, 2017 for PCT Patent Application No. PCT/US2016/060452.

Izzo et al, Radiofrequency ablation in patients with primary breast carcinoma, Cancer, Mar. 2001, 92(8), 2036-2044.

Katritsis et al., Anatomic approach for ganglionic plexi ablation in patients with paroxysmal atrial fibrillation, Am J Cardiol, Mar. 2008, 102:330-4.

Levinson, "Endocardial Microwave Ablation: A New Surgical Approach for Atrial Fibrillation"; The Heart Surgery Forum, 2006.

(56) References Cited

OTHER PUBLICATIONS

Maessen et al., "Beating heart surgical treatment of atrial fibrillation with microwave ablation," Ann Thorac Surg 2002;74:S1307-S1311; retrieved from the Internet on Aug. 19, 2009: http://ats.ctsnetjournals.org/cgi/reprint/74/4/S1307.
Nathan et al., "The junction between the left atrium and the pulmonary veins, An anatomic study of human hearts," Circulation 1966; 34:412-422; retrieved from the Internet on Aug. 19, 2009: http ://circ.ahajournals.org/cgi/reprint/34/3/412.
Po et al, Localization of left atrial ganglionated plexi in patients with atrial fibrillation, J Cardiovasc Electrophysiol, Jun. 2009;20:1186-9.
Pokushalov. et al, Selective ganglionated plexi ablation for paroxysmal atrial fibrillation, Heart Rhythm, Sep. 2009, vol. 6, Issue 9, 1257-64.
Sueda et al., "Efficacy of a simple left atrial procedure for chronic atrial fibrillation in mitral valve operations," Ann Thorac Surg Apr. 1997; 63:1070-1075.
Sueda et al., "Simple left atrial procedure for chronic atrial fibrillation associated with mitral valve disease," Ann Thorac Surg Jun. 1996; 62: 1796-1800.
Wood et al. "Percutaneous tumor ablation with radiofrequency." Cancer 94.2, Jan. 2002, pp. 443-451.
Wu et al. "A randomised clinical trial of high-intensity focused ultrasound ablation for the treatment of patients with localised breast cancer." British journal of cancer 89.12, Sep. 2003, 2227-2233.

\* cited by examiner

SYSTEMS AND METHODS FOR IMAGING AND ABLATING TISSUE

RELATED APPLICATIONS

The present application claims priority to U.S. Provisional Patent Application No. 62/250,676, filed on Nov. 4, 2015 and entitled "Systems and Methods for Imaging and Ablating Tissue," which is hereby incorporated by reference for all purposes.

The present application is related to U.S. Pat. Nos. 7,950,397; 7,942,871; 9,155,588; 8,475,379; 9,033,885; 8,414,508; and 9,192,789; the entire contents of which are incorporated herein by reference.

The present application is also related to U.S. Patent Publication Nos. 2009/0312673; 2010/0049099; 2010/0016762; 2010/0198065; 2011/0257563; 2013/0103064; and 2014/0046313; the entire contents of which are incorporated herein by reference.

The present application is also related to U.S. Provisional Patent Application No. 62/159,531; the entire contents of which are incorporated herein by reference.

BACKGROUND

The present application generally relates to systems and methods for imaging and ablating zones in tissue. More specifically, the present application relates to using an interventional ultrasound catheter to image and ablate tissue. Tissues that may be ablated include cardiac tissue (e.g. for arrhythmias, ventricular tachycardia, atrial fibrillation and flutter, etc.), as well as non-cardiac tissue, such as afferent and efferent nerves (e.g. renal nerves, ganglionated plexi, etc.), tumors, or any other tissue which may be treated by ablation.

Tissue ablation can be used to treat various disease states. An important component of tissue ablation is identifying the target tissue and ablating that tissue, generally without significant damage to surrounding tissues that may be adjacent or collateral to the desired target tissue. As such, it is important to be able to identify both the target and surrounding tissues with an imaging modality, plan the desired lesion based on that information, and execute the planned ablation with a reduced negative impact on non-targeted tissue.

Current ablation devices rely on a number of different imaging modalities for positioning the lesion and/or identifying where the ablation device is located relative to the lesion. Imaging modalities include x-ray/fluoroscopy, electroanatomic mapping, computed tomography (CT), ultrasound, and any combinations thereof. X-ray/fluoroscopy can image the entire body, but has limited spatial resolution, limited soft tissue contrast, and exposes the patient to ionizing radiation. Electroanatomical mapping is used in cardiac ablation applications, but is limited to being a contact technology (for position information), provides no tissue information beyond the tissue surface contact, and spatial resolution is dependent on manual catheter control by the user. Spatial resolution may be improved by merging with CT images; however, the two modalities are typically acquired at different times and are often not easily available. CT images are also not available in a real-time mode. Ultrasound imaging has been used but in general only for target tissue location information provided from a secondary system that is separate from the ablation device.

Ablation devices generally use radiofrequency (RF) as an energy source and cryogenics as a cooling source. These ablation devices rely on secondary imaging modalities for positional information. They do not provide information related to tissue thickness or tissue properties that directly modulate the ablation device. They may have some limited feedback information from the tissue (such as tissue temperature), but none of the current ablation devices provide sufficient information to characterize the target and surrounding tissues and create the lesion with tissue feedback information within a single system. Combinations of the imaging modalities and the ablation devices still do not provide all the useful information to accurately place a lesion to achieve the desired result.

SUMMARY

The present application generally relates to systems and methods for imaging and ablating zones in tissue. More specifically, the present application relates to using a system including an interventional ultrasound catheter to image and ablate tissue, and provides graphical user interfaces to aid in planning, ablating, and assessing the ablation therapy. Tissues that may be ablated include cardiac tissue (e.g. for arrhythmias, ventricular tachycardia, atrial fibrillation and flutter, etc.), as well as non-cardiac tissue, such as afferent and efferent nerves (e.g. renal nerves, ganglionated plexi, etc.), tumors, or any other tissue that may be treated by ablation.

In some embodiments, a user interface system for an ablation procedure includes a display, a controller in electronic communication with the display, a catheter coupled to the controller, and a graphical user interface generated by the controller and shown on the display. The catheter has a distal end comprising an ultrasound transducer, where the ultrasound transducer is configured to emit an ultrasound beam. The graphical user interface includes a three-dimensional anatomical reference map of a chamber of body tissue to be ablated, where a lesion path is superimposed on the anatomical reference map; a catheter position relative to the chamber; and a window showing data. The data includes at least one of a) a distance between the ultrasound transducer and a surface of the body tissue, b) a dosing plan, c) a tissue thickness, and d) a tissue property.

In some embodiments, a method for providing a user interface for an ablation procedure includes providing a user interface system, where the user interface system has a display, a controller in electronic communication with the display, and a catheter coupled to the controller. The catheter has a distal end comprising an ultrasound transducer, and the ultrasound transducer is configured to emit an ultrasound beam. The method also includes generating, by the controller, a graphical user interface shown on the display. The graphical user interface includes a three-dimensional anatomical reference map of a chamber of body tissue to be ablated, where a lesion path is superimposed on the anatomical reference map; a catheter position relative to the chamber; and a window showing data. The data includes at least one of a) a distance between the ultrasound transducer and a surface of the body tissue, b) a dosing plan, c) a tissue thickness, and d) a tissue property.

These and other embodiments are described in further detail in the following description related to the appended drawing figures.

BRIEF DESCRIPTION OF THE DRAWINGS

The novel features of the invention are set forth with particularity in the appended claims. A better understanding of the features and advantages of the present invention will

DETAILED DESCRIPTION

Figure 1:
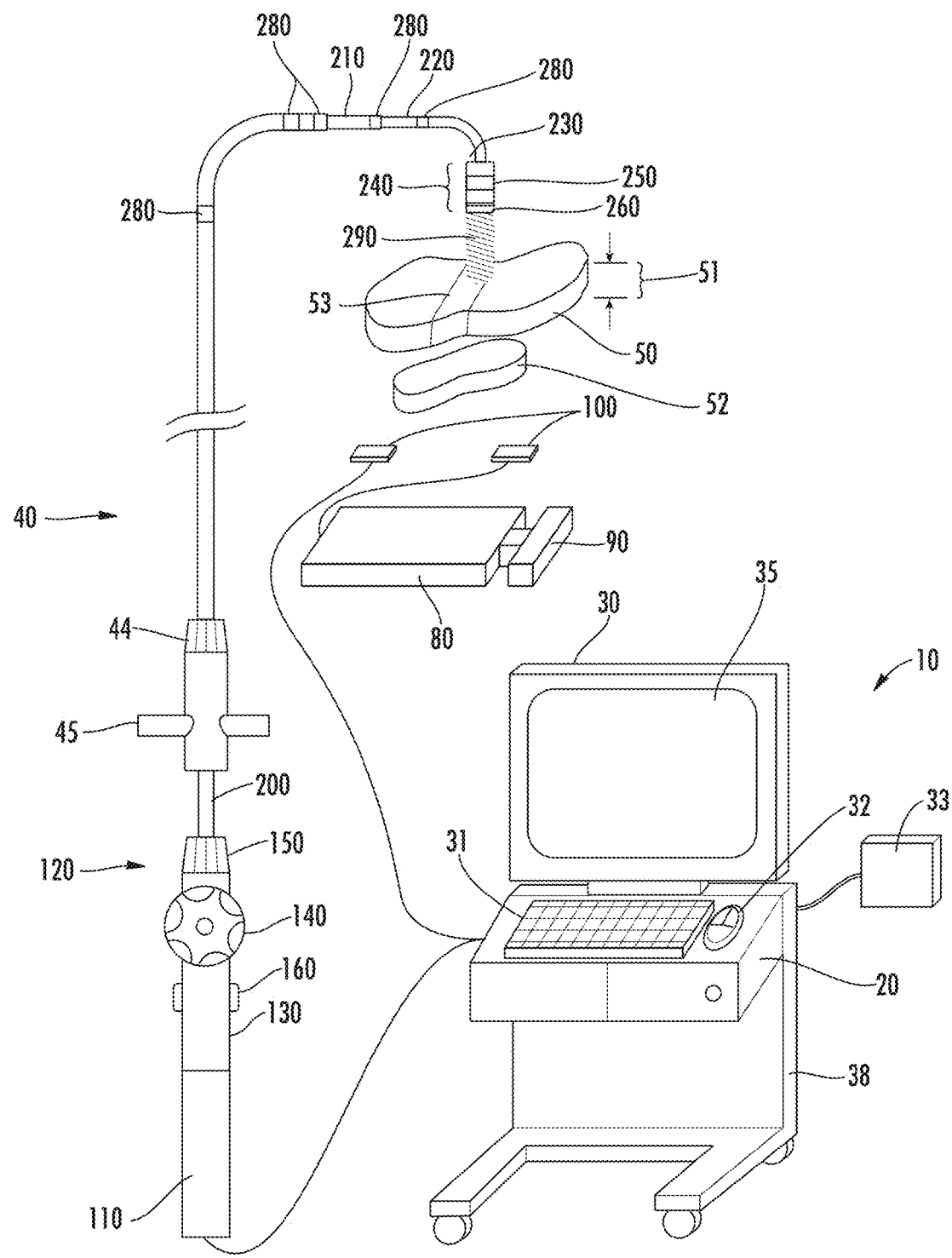
FIG. 1 illustrates an embodiment of the system including sample tissues.

Reference now will be made in detail to embodiments of the disclosed invention, one or more examples of which are illustrated in the accompanying drawings. Each example is provided by way of explanation of the present technology, not as a limitation of the present technology. In fact, it will be apparent to those skilled in the art that modifications and variations can be made in the present technology without departing from the scope thereof. For instance, features illustrated or described as part of one embodiment may be used with another embodiment to yield a still further embodiment. Thus, it is intended that the present subject matter covers all such modifications and variations within the scope of the appended claims and their equivalents.

A catheter-based imaging and ablation system includes a controller, a catheter, and ancillary devices such as those described below. A user interface and software are used to control aspects of the system, such as the display(s), energy delivery, catheter or ancillary device motion control, etc. The display is used to visualize the images and may also serve as a touchscreen to interact with and direct aspects of the system. In some aspects, the catheter-based imaging and ablation system is capable of imaging and displaying any or all of the regional, target, and collateral tissues. The regional tissue generally encompasses an area within which lies at least a portion of the target and nearby collateral tissues. The target tissue is that which is intended to be ablated, and may include regions of the heart, such as for treating atrial fibrillation, atrial flutter, supraventricular tachycardias, Wolff-Parkinson-White syndrome, and ventricular tachycardia, afferent and efferent nerves, such as for ablating renal nerves or ganglionated plexi, carotid bodies, tumors, such as for treating fibroadenoma, and the like. Other target tissues are also contemplated. Collateral tissue is that tissue which lies near the ablation zone that it is not targeted for ablation. This collateral tissue may be identified and demarcated such that the planned lesion avoids this tissue or minimizes heating. Examples of collateral tissue include healthy tissue, and more specifically in the case of treating arrhythmias, may include the esophagus, phrenic nerve, coronary arteries, and internal cardiac structures (papillary muscle, chordae, valves, etc.).

The displayed images and user interface may include a number features, such as 2D or 3D images; color or grayscale coding or other display parameters for distance, tissue type, tissue property (e.g., compressibility, density, stiffness), in-therapy range, out-of-therapy range, motion, angularity to direction of ablation; the ability to manipulate/rotate/zoom any part or all of image; display the catheter, energy source, and or energy/ultrasound beam; display the ancillary devices (sheath, esophageal probe, trocar, port access device, etc.); display the ablation line, zone, depth, width, outline, including error bars (such as ablation width) to indicate spatial uncertainty; display an endocardial map; display an epicardial map; display a tissue thickness map which may include the thickness of the regional, target, collateral tissue on, along, within the lesion path; display ablation parameters at any point or region on, along, or within the planned lesion; workflow steps; system or system component (e.g. catheter) status; and patient, procedure, hospital, and user information. Any or all of these displays and display properties may be used in combination, overlaid, as a transparency, etc.

The capabilities of this system and the associated methods may provide the benefits of increased efficacy, improved ease-of-use, greater safety, reduced procedure duration, reduced user fatigue and error, lower procedure costs, reduced need for repeat procedures, decreased exposure to radiation from imaging systems, etc. compared to existing ablation technologies.

As shown in FIG. 1, a catheter-based imaging and ablation System 10 of the present embodiments includes a Controller 20, a Catheter 120, and ancillary devices. The Controller 20 is operably coupled to the Catheter 120, which may be through the Pod 110. The Controller 20 includes a generator and software, and an integrated or stand-alone Display 30 with a Graphical User Interface (GUI) 35 shown on the Display 30. Also shown in FIG. 1 are input devices such as a Keyboard 31, Mouse 32, and Touchscreen 33, where one or more of these input devices may be utilized in the System 10 along with the associated cabling. In some embodiments, Display 30 may itself include a touchscreen, without the need for a separate Touchscreen 33. Other types of input devices are possible, such as a joystick. The Controller 20 may be mounted on or integral with a Cart 38 or other type of apparatus that enables portability. The System 10 also includes an electromagnetic (EM) tracking system. The EM tracking system includes a Window Field Generator 80, a Window Field Generator Mount 90 and a plurality of electromagnetic sensors. The EM sensors may be located on or within the Catheter 120 and ancillary devices, e.g. EM Sensor 250, as well as a separate sensor or sensors located on or near the patient, e.g. External Sensors 100. The External Sensors 100 may have a wired connection to the System 10 as shown in FIG. 1, or may be wireless.

The Controller 20 through wired or wireless interfaces such as a Display 30, an integral touchscreen or separate Touchscreen 33 or any other suitable Graphical User Interface 35, wired or wireless Keyboard 31 and Mouse 32, joystick, etc. may be used to control aspects of the System 10, such as catheter motion, energy delivery, data inputs and outputs, mapping, planning, pre-therapy, ablation, and post-ablation activities. The Display 30 and Graphical User Interface 35 and control devices will be discussed in greater detail as shown in other figures.

With respect to motion control of the Catheter 120, the Controller 20 controls manipulation of an Inner Shaft Deflecting Section 230 to enable accuracy of motion of Catheter 120 components and an Energy Beam 290. The Controller 20 controls manipulation of the Inner Shaft Deflecting Section 230 through drive mechanisms and optionally incorporates sensors in or near a Catheter Handle 130. The Controller 20 directs movement of these drive mechanisms according to mathematical (algorithmic) models that predict the distal deflection and/or motion in response to movement of the drive mechanisms. These models of the mechanical transfer function may be imperfect, and may result in motion of the Inner Shaft Deflecting Section 230 that deviates from the intended motion, even with feedback provided from sensors reading the drive mechanisms or control cables. Catheter Distal Tip 240 position distortion may be reduced by using the EM Sensors 250 in the Catheter 120 in combination with the Window Field Generator 80 in a closed or semi-closed loop control manner to adjust and modify the actions of the drive mechanisms to correct for any distortion in the motion of the Catheter Distal Tip 240, which houses the energy source, and resultant position and motion of the Energy Beam 290 on a Tissue 50.

The Catheter 120 houses an energy delivery source which is embodied as an ultrasound transducer 260; however, the user interfaces of the present disclosure may also be applied to other types of energy delivery sources. The energy delivery source is operably controlled by both manual and automated and/or semi-automated inputs. Manual inputs are affected directly by the user while automated and/or semi-automated inputs come from the user interacting with the Controller Display 30, Graphical User Interface 35, and as required, Keyboard 31, Mouse 32, Touchscreen 33, joystick, etc. to command operation of certain aspects of the System 10 and procedure.

The Ultrasound Transducer 260 emits an ultrasound beam, such as a collimated beam. The System 10 may include a single energy source, or may alternatively include any suitable number of energy sources. The Ultrasound Transducer 260 may be made of a piezoelectric material such as PZT (lead zirconate titanate) or PVDF (polyvinylidine difluoride), or any other suitable ultrasound emitting material. The Ultrasound Transducer 260 operates at a frequency in the range of 5 to 25 MHz, such as in the range of 8 to 20 MHz, or such as in the range of 8 to 15 MHz.

When energized with an electrical signal or pulse train from the Controller 20, the energy delivery source emits an Energy Beam 290 (such as a sound pressure wave). The properties of the Energy Beam 290 are determined by the characteristics of the energy delivery source which determine the frequency, spectral bandwidth, and pressure amplitude of the Energy Beam 290 (such as a sound wave) propagated into the Tissue 50. The energy delivery source emits an Energy Beam 290 such that it interacts with the target Tissue 50 along a lesion path and forms a Lesion 53. As the Energy Beam 290 travels through the target Tissue 50, its energy is thermal energy. This thermal energy heats the Tissue 50 to temperatures higher than the surrounding tissue resulting in a zone of ablation along the lesion path due to thermal tissue necrosis. The temperatures of the Tissue 50 rise above the temperature where cellular/tissue necrosis occurs and the Tissue 50 is said to be ablated. The lesion may be a complete transmural lesion or substantially transmural. In some embodiments, temperatures of Collateral Tissue 52 are monitored to avoid damage to this non-target tissue. The temperature monitoring may be performed using data from, for example, the Ultrasound Transducer 260, or from a thermocouple or other temperature measurement device on the Catheter 120 or on an ancillary device such as a probe.

The Catheter 120 includes an Inner Shaft 220, an Outer Shaft 200, a Handle 130, and the components thereof. The Inner Shaft 220 proximally (toward the physician) terminates within the Handle 130. The distal region of the Inner Shaft 220 contains one or more EM Sensors 250 for use with the EM tracking system. In some embodiments, an EM Sensor 250 is located on the Inner Shaft 220 near the proximal area of the Inner Shaft Deflecting Section 230. Additional EM Sensors 250 may be located on the Inner Shaft 220, such as in the Catheter Distal Tip 240. The Catheter 120 and ancillary devices may use 5 degree and/or 6 degree of freedom EM sensors. The use of two 5 degree of freedom EM sensors may be used in place of 6 degree of freedom sensors by using a unique software algorithm to determine roll correction.

Figure 2:
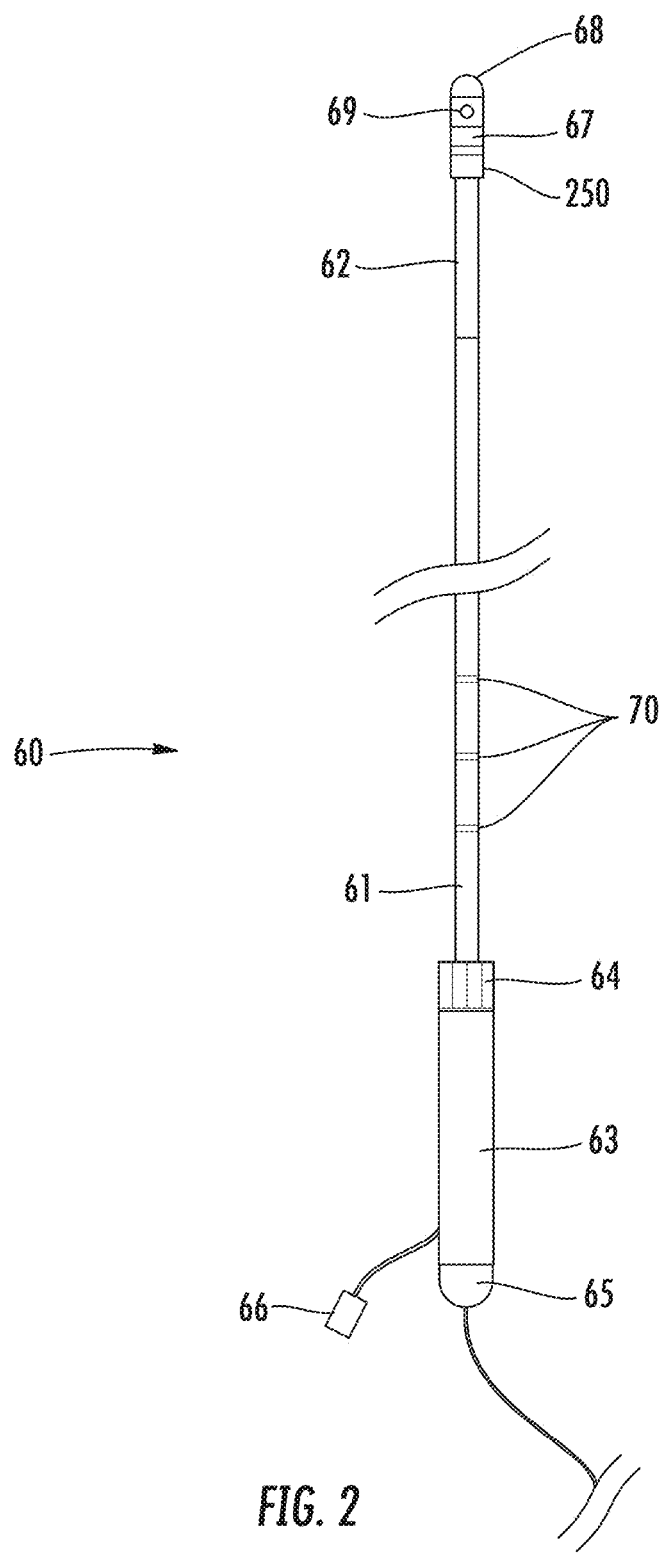
FIG. 2 illustrates an embodiment of an ancillary probe.

FIG. 2 is a plan view of a Probe 60 that may be utilized with the System 10. Probe 60 may be, for example, an esophageal probe, and is comprised of a Probe Shaft 61, optional Probe Deflecting Section 62, and Probe Handle 63. Drive mechanisms within the Probe Handle 63 may actuate control cables to deflect the Probe Deflecting Section 62, such as by rotation of the Probe Deflection Knob 64. The Probe 60 may be provided with multiple functions (e.g. position information, temperature information, electrical information, etc.). The Probe 60 may contain a thermistor or Thermocouple 67 for monitoring temperature of the Tissue 50 or area within the vicinity of the thermistor or Thermocouple 67, one or more EM Sensors 250, and one or more Probe Electrodes 68 that may work in conjunction with the Controller 20 or with separate equipment. These may be connected through a Probe Connector 65. The Probe 60 may also include an Irrigation Port 69 located within the shaft to enable fluid to be introduced from the proximal region, through a Probe Flush Line 66 in the Probe Handle 63, to a more distal region, such as in the region near ablation, which may be used to cool non-target or Collateral Tissue 52. The Probe 60 may also contain Depth Markers 70 on the shaft, which may or may not be radiopaque.

The Probe 60 may be placed in a specific location or moved within a range or positions to obtain positional information that is provided to the operator. This movement allows the Controller 20 to display the position of the Probe 60 or elements of the Probe 60 (e.g. EM Sensor 250) and construct or infer and show the position of a lumen, vessel, tissue, and the like, or portions of, or a position or positions there within. The Probe 60 may be positioned and/or repositioned at any time such that the thermistor or Thermocouple 67 is appropriately placed to monitor temperature of the Tissue 50 (e.g. Collateral Tissue 52), during any part of the procedure, including before, during, and/or after ablation.

Figure 3:
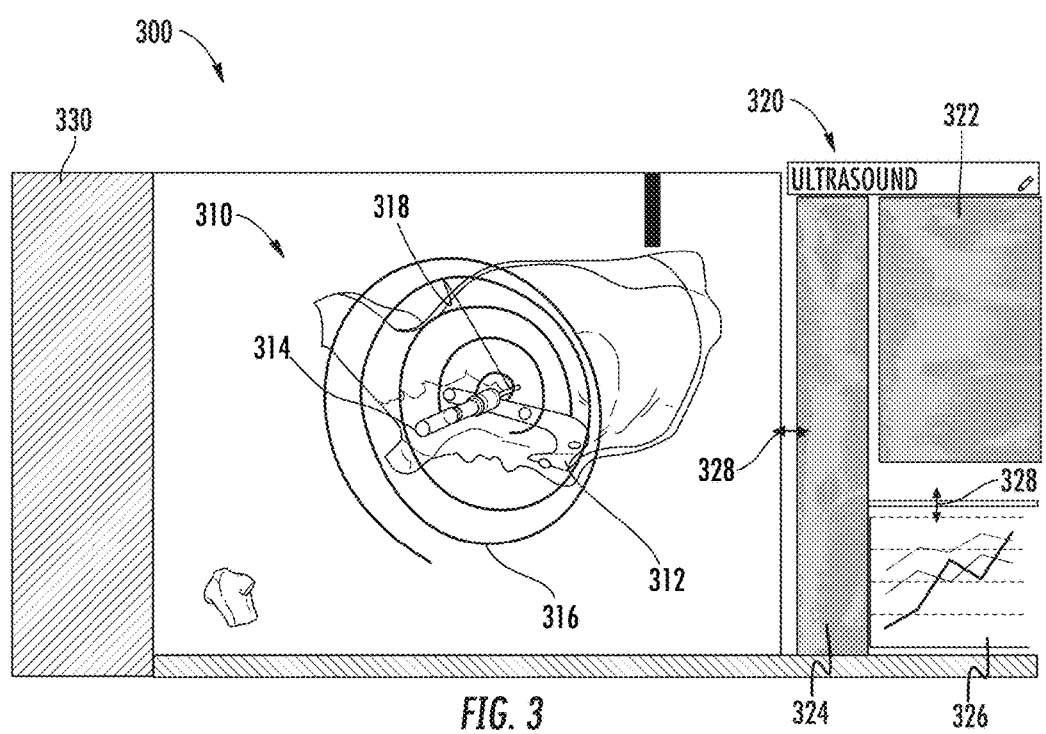
FIG. 3 illustrates an embodiment of a graphical user interface with a 3D map and auxiliary windows.

FIG. 3 shows an example of a Graphical User Interface 300 used with the Keyboard 31, and Mouse 32 (or other control device(s)) during the procedure to enable mapping, planning, pre-therapy scanning, and ablation of the target Tissue 50. Command and control information is displayed, and may provide information to the user, recommend ablation parameters, identify Collateral Tissues 52, enable execution of the ablation parameters through automated or semi-automated control of the Catheter 120, provide feedback from the Controller 20, Catheter 120, Pod 110, and Tissue 50, among other parameters. Graphical User Interface 300 includes a three-dimensional anatomical Reference Map 310 of a chamber of body tissue to be ablated, such as a left atrium. The Reference Map 310 has a Lesion Path 312 superimposed onto it, along with a position of the Catheter 314 and Ultrasound Beam 318 relative to the chamber.

In some embodiments, a Sensing Pattern 316 may also be shown on the Reference Map 310, where the Sensing Pattern 316 is a path which the beam of the ultrasound transducer of the Catheter 314 traverses to gather data about the tissue. The Sensing Pattern 316 is shown as a spiral pattern in this embodiment, but may take other forms such as a raster pattern. The same Ultrasound Transducer 260 may be utilized for both sensing and ablating, and the sensing is performed by operating the Ultrasound Transducer 260 in an amplitude mode (A-mode). A reference map is generated through detecting tissue surfaces from the A-mode sensing while navigating the catheter tip electronically. Conventional intravascular ultrasound imaging techniques use Brightness mode (B-mode), in which a linear phased array of transducers generates two-dimensional image slices that can then be compiled or stacked up into a 3-D image. A conventional phased array forms an image slice by electronic beamforming using the multiple transducers. Use of A-mode sensing with precise control of the ultrasound beam from the catheter tip in the present disclosure is a non-linear, piece-wise or sequential approach to creating a 3D map of the target volume. As the beam from the ultrasound transducer moves along a three-dimensional path (sensing pattern) gathering data, the totality of the transducer positions during the scan essentially forms a virtual array, where the array configuration is defined by the scan sensing pattern. Whereas in conventional B-mode imaging where the received ultrasound data is combined directly to form an image, the A-mode sensing data in the present disclosure is processed to form a set of points located in a 3D coordinate frame defining a point cloud ('PC'). Each point is generated from detecting tissue boundaries and other tissue characteristics such as thickness, volume, and angle of incidence. Tissue boundaries include the endocardial and epicardial surfaces in the heart, and can also include structures beyond the epicardium. Each point in the PC is defined by a 3D vector representing the location and pointing direction of the ultrasound beam. Adjacent points in the PC are combined to form a 3D image, resulting in a 3D surface reconstruction where surfaces can represent the endocardium, epicardium, other anatomical structures, and other tissue characteristics.

Graphical User Interface 300 also includes a Window 320 which can be utilized to display additional information relevant to the ablation procedure, such as distance between the ultrasound transducer and a surface of the body tissue, dosing plan, and tissue thickness. For example, the distance between the ultrasound transducer and a surface of the body tissue may be displayed as a two-dimensional or three-dimensional graph along a sensing pattern traversed by the ultrasound beam of the catheter. For a chamber of body tissue being a left atrium, the surface of the body tissue is the endocardium. Another surface of the body tissue is the epicardium. The dosing plan may be displayed as a two-dimensional graph along the lesion path. The tissue thickness may be displayed as a two-dimensional graph along a sensing pattern traversed by the ultrasound beam of the catheter. Within the tissue thickness display, tissue properties can be displayed including compressibility, density, stiffness, or other properties. Three Panes 322, 324 and 326 are shown in this embodiment, although other numbers of panes such as one, two, or more than three, are possible. The Panes 322, 324 and 326 may be adjustable in size using splitters as indicated by the red arrows 328. Window 320 enables a user to view various aspects about the ablation therapy simultaneously, such as while viewing the 3D Reference Map 310 to navigate the catheter within the chamber for planning or performing the ablation. This simultaneous viewing, including in a combination of 3D and 2D views, improves the efficacy of the ablation procedure and other aspects such as procedure time and user fatigue. In some embodiments, one of more of the views may be displayed in real time, such as providing a live 3D display of catheter navigation on the Reference Map 310, and/or live amplitude mode display of data in Window 320 such as tissue thickness or distance of the ultrasound transducer from the surface of the tissue.

Graphical User Interface 300 may also include a Screen Area 330 for displaying additional information about the procedure, such as session information, workflow steps, procedure information, patient information, hospital information, and user information. Procedure information can include, for example, total time, lesion creation time, and time remaining to create the lesion. Workflow steps may include, for example, mapping, planning, dosing, and ablation/therapy.

The Graphical User Interface 300 also provides a graphic of the Ultrasound Beam 318 in 3D. The beam graphic can aid the physician in having a better understanding of the 3D geometry that is inherent to non-contact based ablation. Showing the Ultrasound Beam 318 allows the user to gain intuition on catheter position and beam direction in relation to anatomical targets. Depiction of the direction of Ultrasound Beam 318 can be derived from EM sensors 250 on Catheter 120 that provide positioning information on the location and angle of the catheter tip. Positioning information can be utilized from other sources as well, such as ultrasound information from the Ultrasound Transducer 260 and Radiopaque Markers 280 on the Catheter 120.

The Graphical User Interface 300 is illustrated as having the anatomical Reference Map 310 bordered on the left and right by the Screen Area 330 and the Window 320, respectively. However, the arrangement of these areas can be altered in various embodiments, such as in horizontal or vertical alignment, overlapping with each other, varying in size relative to each other, or being adjustable in size. In addition, the Reference Map 310, Screen Area 330, Window 320 and Panes 322, 324 and 326 may be configured as widgets that can be customized according to user preferences or for specific workflow practices of a particular medical facility.

Figure 4:
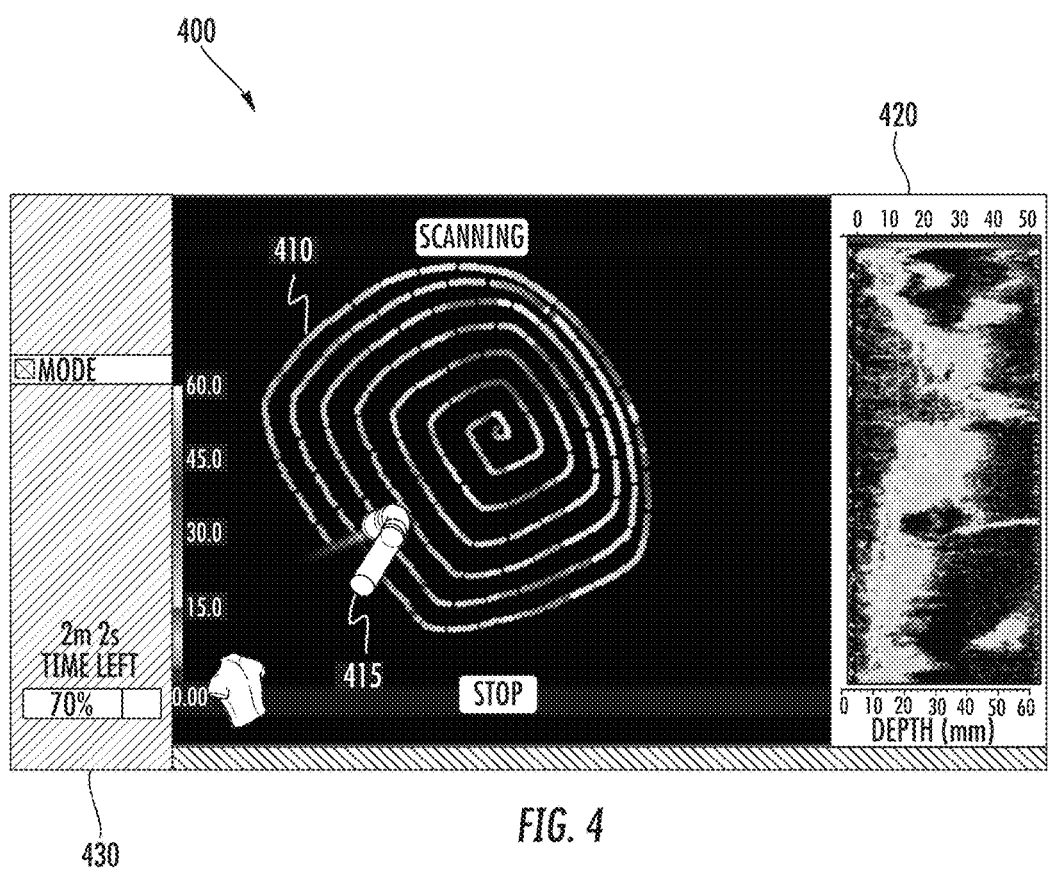
FIG. 4 illustrates an embodiment of another graphical user interface showing a 3D scanning map and 2D ultrasound data window.

FIG. 4 is an example of a Graphical User Interface 400 for live acquisition when a scan of an area is being acquired by the Ultrasound Transducer 260 of the Catheter 120. This acquisition can occur during multiple time points within the workflow. Graphical User Interface 400 includes a Live Scan Image 410, which may be generated from, for example, data on endocardial points taken along a sensing pattern, which is a spiral pattern in this embodiment. The Live Scan Image 410 can be depicted in color or grayscale to indicate parameters being measured such as distance from the ultrasound transducer or tissue thickness. A real-time Catheter Representation 415 is displayed, which actively updates on the display as the catheter navigates along the scanning path. Window 420 shows live data from the active scan, which may be a two-dimensional display of motion mode (M-mode) data as illustrated for tissue thickness in this example. A Screen Area 430 displays estimated remaining time for the scan to be completed in this example, along with a scan progress bar indicator and percent remaining indicator.

In some embodiments, a graphical user interface screen similar to that of FIG. 4 may be utilized to customize a scan pattern. For example, the Live Scan Image 410 of FIG. 4 could be replaced by a proposed scan shape, where the screen includes tools for the user to edit the shape of the scan pattern. For example, the shape may be edited to change a resolution level, such as a coarse scan to a higher resolution scan. The shape may also be edited for overall size, dimensions and aspect ratio. The editing tools may be in the form of numerical value inputs, slider tools, drop-down menus, and the like, and combinations thereof.

Figure 5:
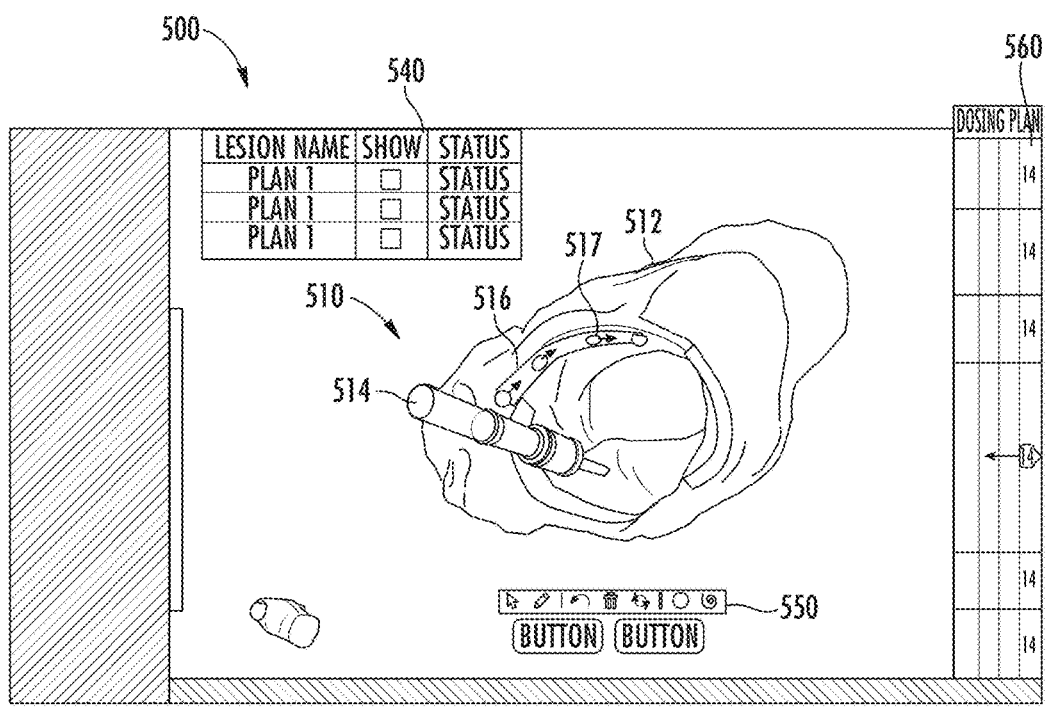
FIG. 5 illustrates another embodiment of a graphical user interface showing a lesion overlay map and a dosing plan.

FIG. 5 is an embodiment of a Graphical User Interface 500 which shows an anatomical reference map as a Lesion Overlay Map 510. The Lesion Overlay Map 510 shows the chamber of Body Tissue 512 with a Catheter 514 and Lesion Path 516. Graphical User Interface 500 also includes an Overlay Window 540 in which different lesions paths can be planned. In this example, three lesion paths—plan 1, plan 2, and plan 3—are listed. Using the Overlay Window 540, the user can select or toggle which lesions to show on the Graphical User Interface 500. That is, one or more lesion paths can be drawn, viewed and modified on the screen at one time. The status of each lesion plan can also be displayed, where the status may include: delivered (successfully completed), canceled (canceled by user or software), or pending (available plan for ablation). The Graphical User Interface 500 thus is able to display lesion paths that have been completed and others that have been planned.

The lesion paths may be planned using a tool, such as a Toolbar 550, on the Graphical User Interface 500. The Toolbar 550 can include buttons to enable options such as selection mode to select or deselect the active plan or points on the active plan; editing mode to add, move, or insert points in lesion segments; undo change; clear plan; reverse path; or lesion touch-up to add pre-defined shapes to the active map. The lesion planning Toolbar 550 allows the user to plan a lesion path using a selection option such as free-form drawing, segmented drawing, choosing from a stored catalog of lesion paths, and modifying a displayed lesion path. Free-form drawing involves the user manually drawing the path by, for example, guiding a cursor with a mouse or joystick. Segmented drawing involves the user clicking locations on the Lesion Overlay Map 510 to set Anchor Points 517 along the lesion path, and the computer software in the Controller 20 connects the lesion path segments between the Anchor Points 517. The stored catalog option enables a user to select lesions paths that are stored in the system (i.e., in a memory unit of the Controller 20), where in some embodiments the system can recommend one or more lesion paths to the physician.

As the lesion path is planned and modified, the system can update the lesion parameters on the display. The lesion parameters can include dosing parameters, such as energy to be delivered to the target tissue and speed at which the ultrasound beam moves along tissue surface following the lesion path. In some embodiments, the lesion path is planned after the catheter has been positioned within the body, while in other embodiments the system (e.g., Controller 20) can recommend a catheter position after the lesion path has been planned.

Graphical User Interface 500 also includes a Dosing Plan Window 560, which is shown as a template for a 2D graph of dose along the lesion path in this illustration. The dosing plan depicts the energy density level to be delivered for each lesion segment, where the system can highlight the current segment being treated during ablation. The dosing can be confirmed on a separate user interface screen, allowing the user to inspect the recommended dose and associated ultrasound data for the active plan. On such a dosing confirmation screen, the user can modify the dose per segment for an active plan.

Figure 6:
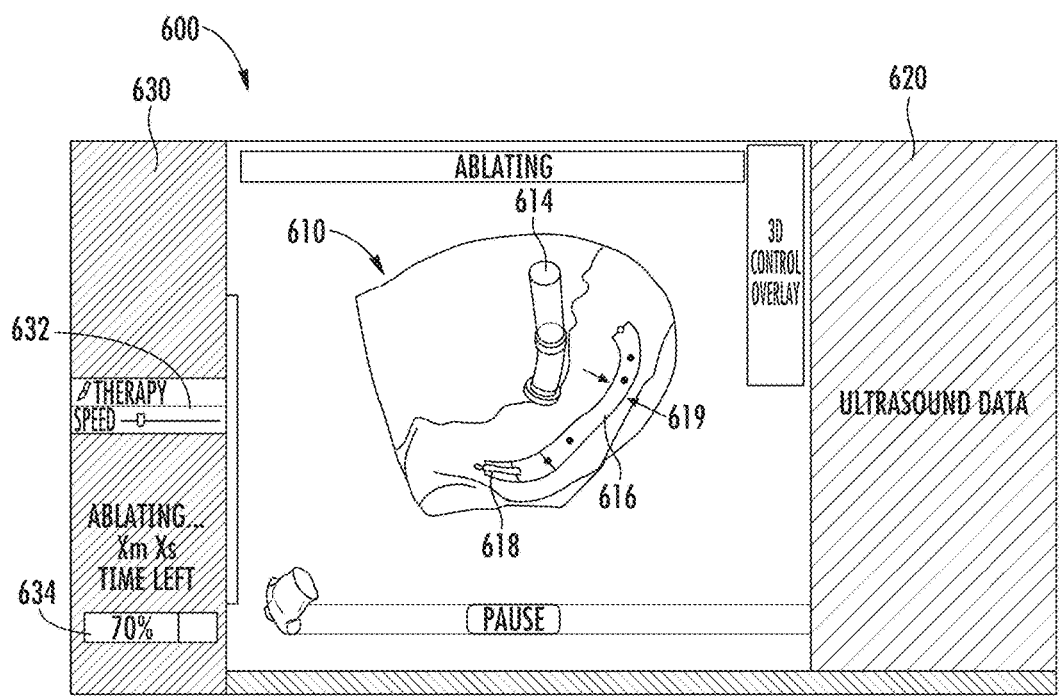
FIG. 6 illustrates an embodiment of a graphical user interface showing an ablation map.

During ablation, a Graphical User Interface 600 as shown in FIG. 6 may be utilized. The Graphical User Interface 600 is an active ablation screen used in therapy mode, showing the progress of ablation and allowing the user to take actions such as manipulating the speed factor or to pause ablation. A speed factor allows a real-time adjustment to the delivered dose as slower speeds increase the effective dose while faster speeds decrease the effective dose. A 3D anatomical Reference Map 610 shows a close-up view of a region of the chamber being ablated in real-time by a Catheter 614, along the Lesion Path 616. A Lesion Progress Indicator 618 is a visual depiction of the ablation progress along the active lesion path. The Screen Area 630 in this embodiment includes an interface to change a Speed Factor Value 632, depicted here as a slider interface. The Screen Area 630 also has an Ablation Progress Indicator 634, embodied here as a bar indicator labeled with the percent of therapy duration remaining along the planned path.

In some embodiments, the anatomical Reference Map 610 is a color map to depict an ablation range of the Catheter 614, where the ablation range includes an in-therapy range and an out-of-therapy range. For example, a green, cyan, blue, or purple color may indicate tissue that is near enough to the catheter tip to be affected by the heat generated by the ultrasound beam, while a yellow or red color indicates tissue that is too far to be effectively treated. Different colors can also represent distances from the catheter tip as being either in-therapy range or out-of-therapy range. In some embodiments, the Graphical User Interface 600 displays ablation parameters such as dose, speed, and temperature at any point on the image or along any portion of the lesion path. These parameters may be displayed on Reference Map 610, in Screen Area 630, or in Window 620 including auxiliary panes within Window 620. Based on the ablation parameters and motion of the Catheter 614, a depiction of a Lesion Path Width 619 may also be displayed on the Graphical User Interface 600. In some embodiments, the Anatomical Reference Map 610 further includes displaying collateral tissue to allow the user to monitor and avoid damage to the collateral tissue.

The controller of the ablation system (e.g, computer hardware and software of Controller 20) uses a unique algorithm to compute the delivered dose along the Lesion Path 616. This algorithm can be used prior to the start of ablation to compute a recommended dose, and can be used during ablation to compute the actual delivered dose. During ablation, the controller may use delivered dose results to adjust system parameters to maintain the target dose specified by the user. After ablation, a graphical user interface similar to that of Graphical User Interface 600 may display a graphical representation of the delivered dose. This graphical representation may be a 3D depiction of the delivered dose or a simplified 2D depiction along the lesion path. The post-ablation delivered dose graphic can also indicate areas where the delivered dose deviated from the user specified dose.

The position of the catheter can also be actively monitored and controlled during therapy. For example, the system can mark and/or record the navigation history of the catheter, storing locations where the catheter has delivered energy. In some embodiments, the graphical user interface displays a spatial uncertainty of the lesion path or zone, such as by monitoring movement of the catheter and/or movement of the tissue. In some embodiments, at least a portion of the catheter is moved by the system to ablate the body tissue along the lesion path. That is, the system analyzes the position of the catheter, such as by EM sensors on the catheter, and controls the catheter navigation along the planned lesion path. The analysis of the catheter position can include not only a vertical and lateral distance from the lesion path, but can also include an angle of the distal tip of the catheter so that dosages can be adjusted to account for angles of incidence (AOI) of the ultrasound beam relative to the tissue surface.

The Display 30 and Graphical User Interfaces 300, 400, 500 and 600 may show a number of features, such as a 2D or 3D image or map, which may be in color, grayscale, or any combination. The Display 30 may use various colors or shades to represent distance to the Tissue 50 or tissues from the energy source. Additionally, colors and shades may be used to demarcate, for example, Tissue 50 type, if a Tissue 50 or tissues are within ablation range of the energy source; out-of-ablation range; amount or type of motion; angularity of the Energy Beam 290 to a Tissue 50 or tissues. The user interfaces can provide the ability to manipulate/rotate/zoom any part or all of image; display the Catheter 120, energy source, and or energy/ultrasound beam; and display the ancillary devices (Sheath 40, esophageal probe, trocar, port access device, etc.). The user interfaces provide the ability to display the ablation line, segment, zone, depth, width, outline, including error bars (such as line width) to indication uncertainty; display an endocardial map; display an epicardial map; display a tissue thickness map which may include the thickness of the regional, target, Collateral Tissue 52 on, along, within a lesion segment or the entire the lesion path; display ablation parameters at any point or region on, along, or within the planned lesion; display a lesion overlap; or status of the System 10 or System 10 component (e.g. Catheter 120). Any or all of these displays and display properties may be used in combination, overlaid, as a transparency, tiled, be available as pages, etc. At any point in time or continuously, any and all System 10 information can be stored in the System 10 or externally for retrieval and archiving.

The graphical user interfaces of the current embodiments are able to present ablation planning and therapy information in unique ways compared to conventional systems. In contrast to other 3D mapping systems, for example, where the map is static and the catheter location is some form of filtered positional representation, the maps of the graphical user interfaces disclosed herein can display a more accurate view of relative characteristics between the tissue and catheter. Characteristics include distance between the catheter tip and tissue, angle of incidence (AOI) and effective tissue thickness. Effective tissue thickness is the actual tissue thickness through which the beam will traverse due to the AOI of the catheter tip relative to the tissue surface. Tissue properties detected by the ultrasound beam can also be overlaid on the 3D map to inform the user about properties that could inform improved dosing by adjusting recommended dose settings. The present systems and methods can convey statically an assessment of characteristics across the cardiac cycle in a simplified GUI. For example, statistical measures of characteristics can be displayed on a static map rather than showing a cyclic, time-varying, value of a given characteristic. A static map may be embodied as, for instance, a static image of the catheter position or of the data shown in the window, where the catheter position or the data is filtered over a cardiac cycle, such as being synthesized for a single cardiac phase, or synthesized over a portion of or all phases of a cardiac cycle. The synthesis of information can represent an average, maximum, minimum, or other statistical measures. In other embodiments, a dynamic map of the catheter position or of the data shown in the window may be displayed, where the dynamic map is an animation of a family of 3D maps for select cardiac phases. By utilizing static or select dynamic images, visual fatigue is reduced compared to displaying continuously-varying data to the user. Statistical measures can include displaying the average, minimum, maximum, variance, or range on the static map.

In addition to displaying a single characteristic at a time, the present graphical user interfaces can present a system-derived characteristic that is synthesized from two or more direct measures. For example, the distance between the catheter and tissue can be combined or correlated with the angle of incidence information to convey regions on the map that are ideal for lesion delivery. The graphical user interface thus can include a displayed combined characteristic, where the combined characteristic is based on combining ultrasound information from the sensing ultrasound beam with position information from the electromagnetic sensors of the catheter. The ultrasound information that may be used in formulating the combined characteristic can include at least one of an angle of incidence, an effective tissue thickness, a tissue property, and the distance between the ultrasound transducer and a surface of the body tissue. This information could be conveyed for the current catheter location, or displayed for a user-defined virtual catheter position. Thus, the presentation of graphical information as described in the present embodiments aids in optimal catheter placement for performing ablation efficiently.

The unique graphical user interfaces are based on unique underlying data acquisition methods and algorithms. In some embodiments, data synchronization from multiple sensors allows the present systems to display all associated data elements in a time-synchronized fashion in the graphical user interface. For example, ultrasound data can be used in combination with position information from EM sensors on the catheter. Deriving the orientation of the catheter by utilizing EM sensor information enables displaying of unique information such as beam angle of incidence to the tissue. This is done in real-time during a scan or ablation, and/or in a non-real-time way after a scan or ablation completes. In some embodiments, data processing algorithms also include a motion-corrected view of the data.

In various embodiments, additional ablation aspects may be computed and displayed in 2D and/or 3D representations of the graphical user interfaces of the present disclosure. For example, the graphical user interfaces can include an edema map which is a map showing areas of tissue swelling due to thermal injury. The edema map can show the differences before and after ablation, based on tissue thicknesses derived from ultrasound data collected by the ultrasound transducer of the catheter. In another example, the graphical user interfaces can support the re-doing of a procedure. When a patient requires a repeat procedure, the software can display on the graphical user interface a summary of the prior procedure, showing delivered lesions and associated imaging data. This data can be registered to a new map and help guide the redo procedure. The system may present a set of difference maps and graphical displays to highlight changes in the state of the anatomy between the original and repeat procedures.

Figure 7:
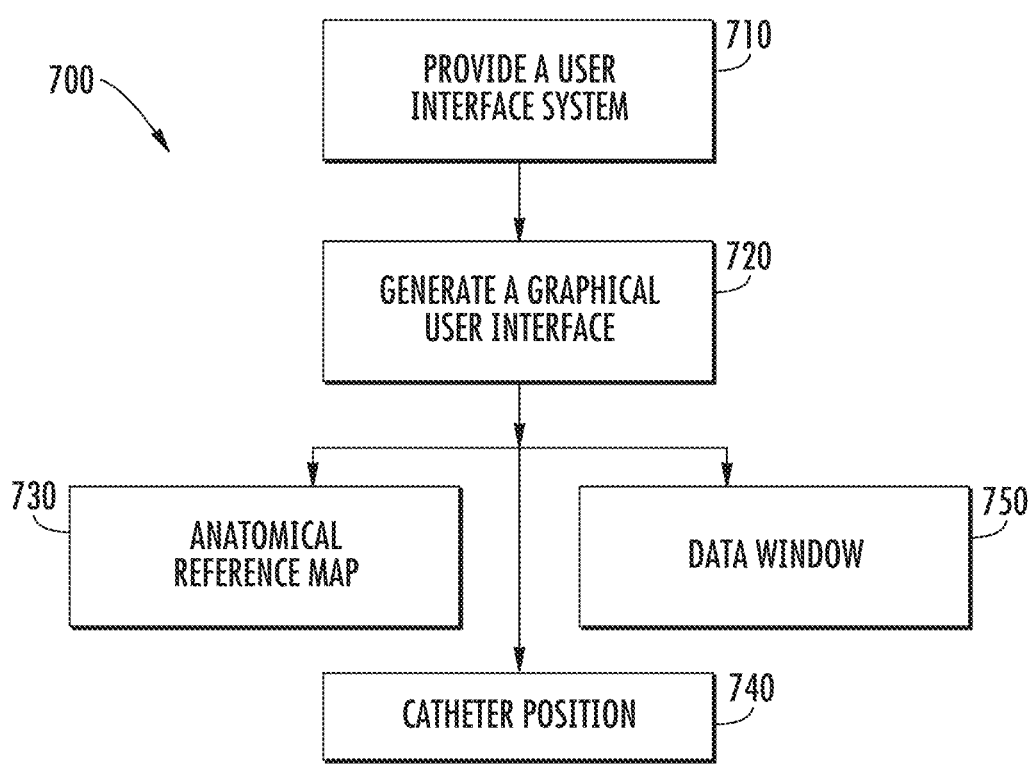
FIG. 7 illustrates a flowchart of methods of providing a user interface for an ablation procedure, according to the present embodiments.

FIG. 7 is an example flowchart 700 of methods for providing a user interface for an ablation procedure. Note that although flowchart 700 and the methods and systems throughout the present disclosure are described in relation to cardiac ablation, the present embodiments may also be applied to non-cardiac tissue, such as afferent and efferent nerves (e.g. renal nerves, ganglionated plexi, etc.), tumors, or any other tissue that may be treated by ablation. In step 710, a user interface system is provided, where the system includes a Display 30, a Controller 20 in electronic communication with the Display 30, and a Catheter 120. The Catheter 120 is coupled to the Controller 20, and the Catheter 120 has a distal end, such as Distal Tip 240 in FIG. 1, comprising an Ultrasound Transducer 260. The Ultrasound Transducer is configured to emit an ultrasound beam, such as Energy Beam 290. The Catheter 120 can include a plurality of electromagnetic sensors, such as with five or six degrees of freedom, to provide position tracking information of the catheter tip.

Step 720 involves using the controller to generate a graphical user interface to be shown on the display. The graphical user interface includes a three-dimensional anatomical reference map 730 of a chamber of body tissue to be ablated, where a lesion path is superimposed on the anatomical reference map. In some embodiments, the anatomical reference map is generated from ultrasound information collected in an amplitude mode along a sensing pattern traversed by the ultrasound beam of the catheter. The distal end/tip of the catheter may be moved by the controller to ablate the body tissue along the lesion path. The graphical user interface also displays a catheter position 740 relative to the chamber, and a window 750 showing data. In various embodiments, the graphical user interface of step 720 is configured as, although not limited to, the Graphical User Interfaces 300, 400, 500 and 600 as described above.

The data includes at least one of a distance between the ultrasound transducer and a surface of the body tissue, a dosing plan, a tissue thickness, and a tissue property. The tissue property is one of compressibility, density, and stiffness. The data may be based at least in part by information collected by the Ultrasound Transducer 260, where the ultrasound transducer operates in amplitude-mode. In some embodiments, the anatomical reference map 730 is a 3D image, while the data window 750 is a 2D image. For example, in some embodiments the distance between the ultrasound transducer and the surface of the body tissue is displayed as a two-dimensional graph along a sensing pattern traversed by the ultrasound beam of the catheter; the dosing plan is displayed as a two-dimensional graph along the lesion path; and the tissue thickness is displayed as a two-dimensional graph along a sensing pattern traversed by the ultrasound beam of the catheter. Tissue properties can be overlaid on top of the tissue thickness display and toggled on or off. In some embodiments, the system may also automatically detect and display extra-cardiac structures in the image data and highlight them in the graphical user interface (e.g., an M-MODE image) and in 3D in relation to the echo anatomical map and lesion path. In some embodiments, collateral tissue may be displayed on the 3D anatomical reference map and/or in the data window.

In some embodiments of the methods of flow chart 700, the anatomical reference map is displayed as a color map of an ablation range of the catheter, where the ablation range includes an in-therapy range and an out-of-therapy range. Some embodiments may include displaying, on the graphical user interface, ablation parameters at any point on the image or along any portion of the lesion path. Ablation parameters include, for example, dose, speed, and temperature. One or more of the elements of the graphical user interface of step 720 may be displayed in real-time; that is, with live data. For example, the generating of a graphical user interface can include displaying the catheter position or the data shown in the window in real-time.

In some embodiments, the catheter position or the data shown in the window are a static image synthesized over one or more phases of a cardiac cycle. In other embodiments, the catheter position or the data shown in the window may be displayed as a dynamic image. In some embodiments, the graphical user interface includes a tool that allows a user to plan a lesion path using a selection option. The selection options include free-form drawing, segmented drawing, choosing from a stored catalog of lesion paths, and modifying a displayed lesion path. Optionally, the controller can recommend a position of the catheter relative to the lesion path. The graphical user interface can also include a spatial uncertainty of the lesion path or lesion zone.

In some embodiments, at least a portion of the catheter is moved by the controller of the system to ablate the body tissue along the lesion path. The movement of the catheter is determined by the lesion path planned by the user and/or system, using parameters that have been calculated from the anatomical reference map and ultrasound data. For example, the system may establish a position and angle of the ultrasound beam (Energy Beam 290) from the catheter based on angles of incidence and tissue thicknesses to achieve a specific dose along the lesion path, while also considering the anatomical geometry of the chamber being treated and any nearby collateral tissue.

In some embodiments, the catheter has a plurality of electromagnetic sensors, and a combined characteristic is displayed on the GUI where the combined characteristic is based on combining ultrasound information from the ultrasound transducer with position information from the electromagnetic sensors. The ultrasound information may be at least one of an angle of incidence, an effective tissue thickness, a tissue property, and the distance between the ultrasound transducer and a surface of the body tissue.

Features and use of the System 10 of FIG. 1 will now be described as part of an ablation procedure, such as imaging and ablation for treatment of atrial fibrillation in the left atrium in this example.

The Window Field Generator 80 is placed in position, in this example, under the catheterization table and held in position by the Window Field Generator Mount 90. At least one External EM Sensor 100 is placed on the patient as a reference point. Multiple EM Sensors 100 may be used to improve spatial tracking and monitoring of EM field points. The Controller 20 interrogates the EM field and determines if a good signal and accurate location of the External EM Sensors 100 and EM Sensors 250 is achieved or not. This information is provided to the user on the Display 30. If a good signal is not achieved, the user can move the patient or the Window Field Generator 80 to achieve a good position which will be indicated on the Display 30.

An introducer is inserted into the patient's femoral vein. Transseptal access is gained through standard percutaneous techniques. The Sheath 40 is inserted through the introducer and advanced. The Sheath 40 may be deflected by rotation of the Sheath Deflection Knob 44 to accommodate atraumatic placement of the Sheath 40 across the septum. The Deflection Knob 44 may be used to fine tune the angle of the Sheath 40 through the septum. The Sheath 40 may then be engaged within the Sheath Stabilizer 45 to maintain position of the Sheath 40 throughout the procedure.

The Catheter 120 is introduced through the Sheath 40 and advanced until the Outer Shaft Deflecting Section 210 exits the Sheath 40. The Outer Shaft Deflecting Section 210 may be deflected using the Manual Deflecting Knob 140, rotated using the Manual Rotation Knob 150, and/or the Catheter 120 may be advanced or retracted to grossly align the Catheter Distal tip 240 pointing at the region of interest. The Inner Shaft 220 is advanced using the Slider 160 until the Inner Shaft Deflecting Section 230 extends out of the distal end of the Outer Shaft 200. This can be accomplished by visualizing the Radiopaque Markers 280 on the Inner Shaft 220 and Outer Shaft 200.

The Probe 60 may be flushed through the Irrigation Port 69 and then introduced, in this case into the esophagus, and positioned using the Depth Markers 70 to where the distal end of the Probe 60 is roughly aligned with the heart. The Probe 60 is connected to the Controller 20, and the Controller 20 interrogates the Probe 60 for accurate positional information from the EM Sensor 250 in the Probe 60, connectivity from the Thermocouple 67, and other connections as applicable (e.g. Probe Electrode 68). The Graphical User Interface 300 (or Graphical User Interfaces 400, 500, 600, or other embodiments of these interfaces) may be used to select obtaining positional information from the Probe 60 to obtain a map of the Probe 60 location. Upon selecting this feature, the Probe 60 is moved and the Controller 20 acquires the positional information from the EM Sensor 250. The Controller 20 compiles the information and creates a map depicting where the Probe 60 moved. Mapping with the Probe 60 may be conducted or repeated at any time.

The user, using, for example, the Graphical User Interface 400 and control inputs, directs the System 10 to perform a mapping scan of the left hemisphere of the left atrium. This is accomplished by inputs on the Controller 20 initiating ultrasound and having the drive mechanisms in the Pod 110, or directly in the handle or Controller 20, direct the handle to deflect the Inner Shaft Deflecting Section 230 to steer the Catheter Distal Tip 240 and Energy Beam 290 in a specific pattern to obtain ultrasound information of the Tissue 50 and positional information, without the energy source being in contact with the Tissue 50.

Figure 8A:
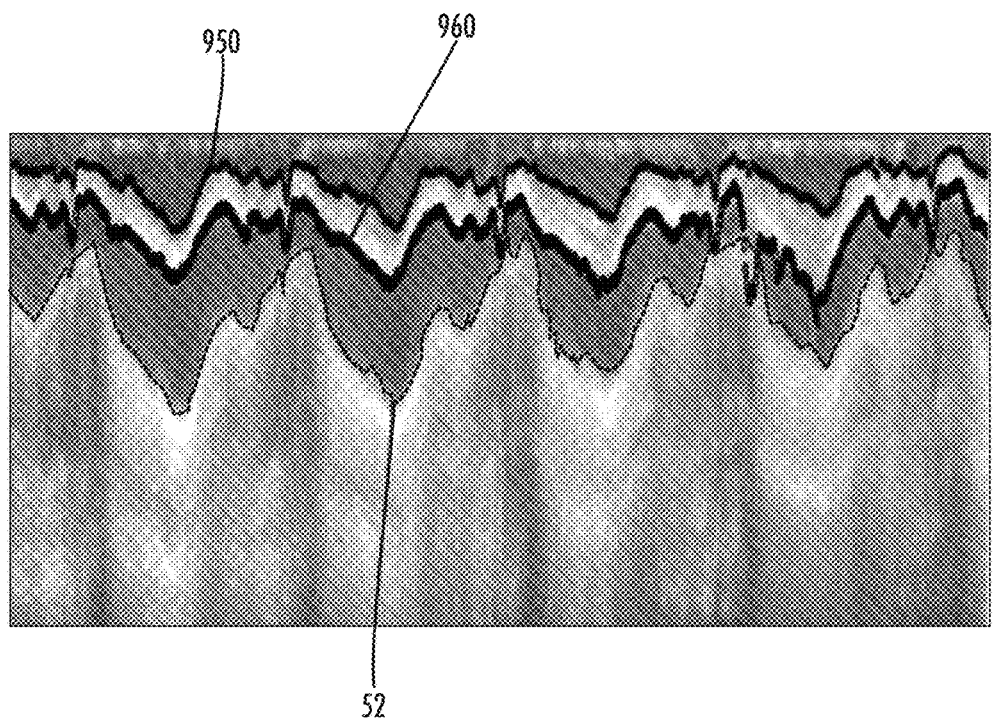
FIGS. 8A-8C illustrate embodiments of 2D ultrasound maps in which tissue layers are identified.

From a scan and the captured ultrasound reflections, the mapping capabilities of the System 10 uniquely employ algorithms to determine the distance to various Tissues 50. For example, the Ultrasound Transducer 260 may take measurements in amplitude mode (A-mode), where the data is analyzed by the Controller 20 and converted into visual graphs for viewing by the user. FIG. 8A shows the ultrasound signal and the software-identified Endocardium 950, Epicardium 960, and Collateral Tissue 52 displayed in a two-dimensional graph along the path of the scan. In the example of FIG. 8A, the Endocardium 950 is derived from the first significant reflection or echo, the Epicardium 960 from the second significant reflection or echo, and Collateral Tissue 52 from additional reflections). In addition, Tissue 50 type(s) (properties of the reflection), Tissue 50 motion, the rate of motion, angularity to the Tissue 50(s) may also be derived. The identified distances from the energy source may also be added to or subtracted from each other or a reference point by the software. For example, subtracting the distance from the energy source to the epicardial surface from the distance from the energy source to the endocardial surface provides a Tissue Thickness 51 (as shown in FIG. 1) of the myocardium.

Figure 8B:
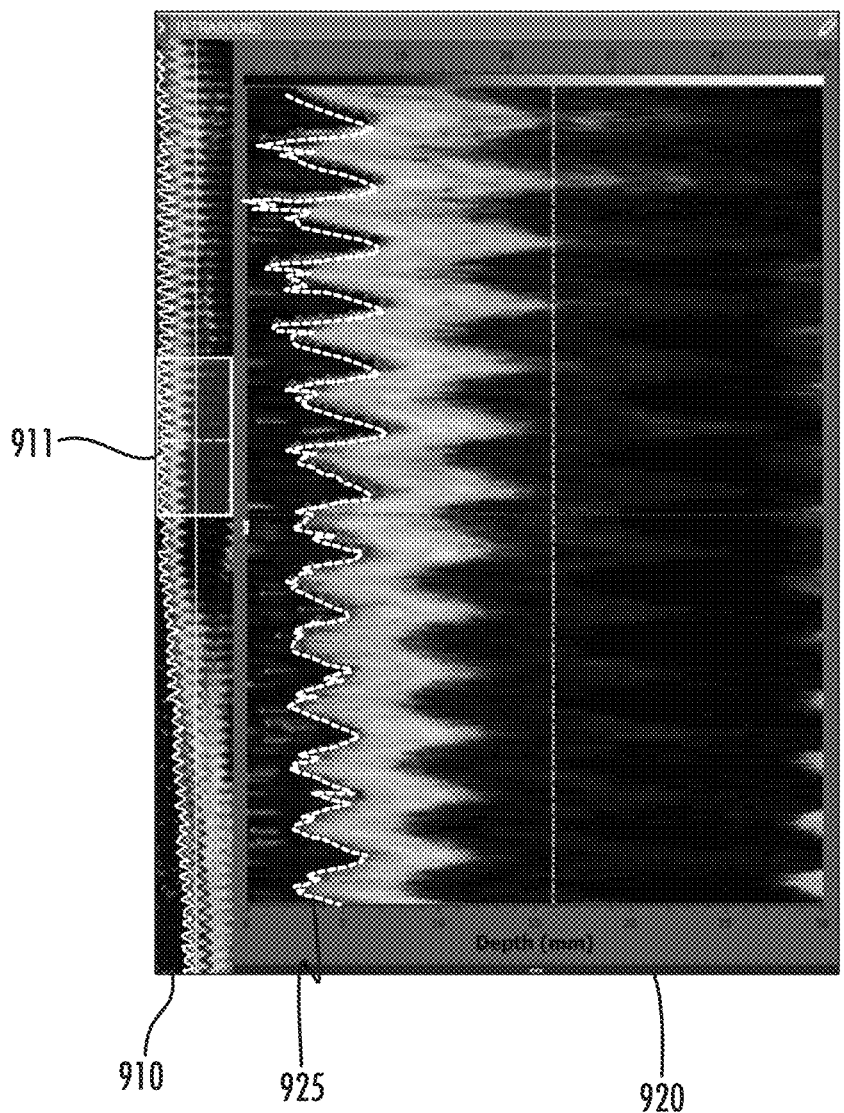
Figure 8C:
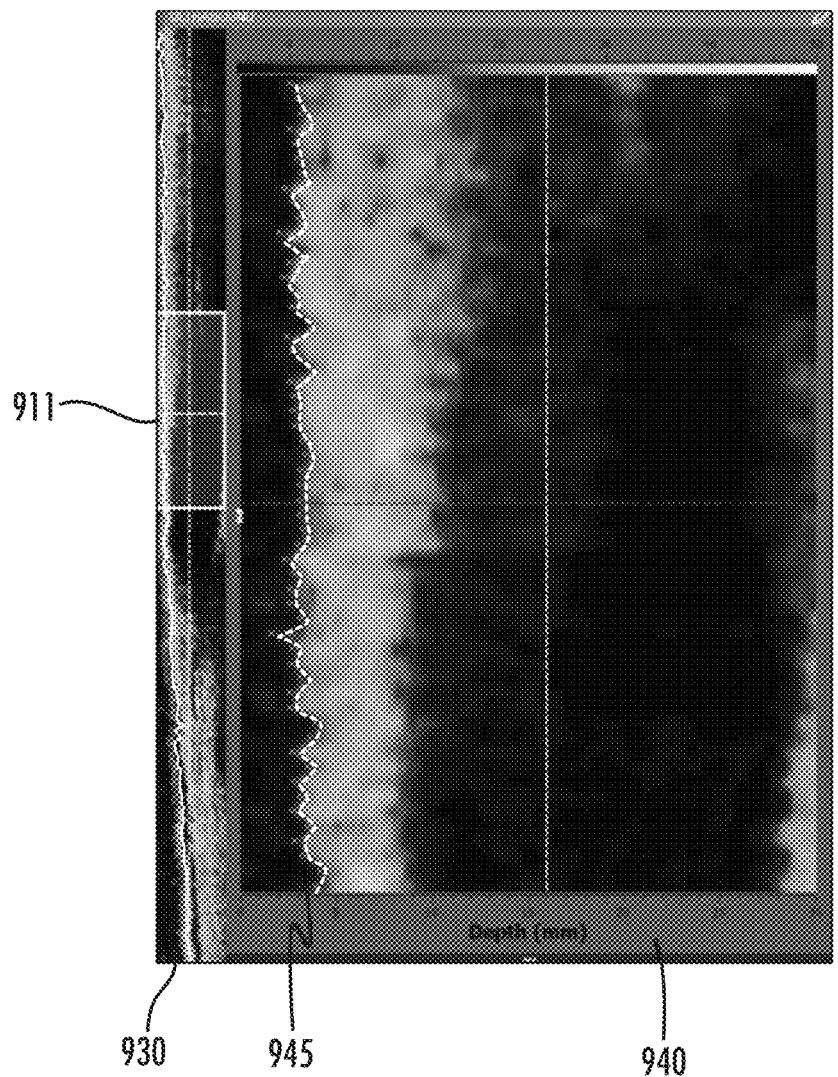

FIGS. 8B and 8C illustrate motion correction that may be performed and displayed according to some embodiments. FIGS. 8B and 8C show ultrasound reflections in M-Mode similar to that of FIG. 8A. FIG. 8B utilizes a full data set while FIG. 8C represents a motion-corrected data set, where endocardial border detection is shown in this example of FIGS. 8B and 8C. In FIG. 8B, Window 910 shows ultrasound data over an extended portion of the scanning path, and Window 920 is a close-up view of the Segment 911 of Window 910. The Endocardium 925 is identified, being derived from the first significant ultrasound reflection or echo. FIG. 8C similarly has a Window 930 showing ultrasound data over the extended portion of the scanning path, and a Window 940 showing a close-up of the Segment 911 of Window 930. The ultrasound information in Windows 930 and 940 have been corrected for motion, such as motion due to cardiac and respiratory cycles. As can be seen, the representation of Endocardium 945 is more realistic than Endocardium 925, with Endocardium 945 having a smoother surface than the pulsed depiction of Endocardium 925. Thus, the graphical user interfaces and methods of the present disclosure can provide more accurate data on which to plan and execute ablation procedures by accounting for motion.

By using the positional and directional information obtained during the scan from the pull wire position, EM Sensors 250 position, and the ultrasound signal at all positions; the software in the Controller 20 constructs an image or images that may then be shown on the Display 30 and be used as part of the graphical user interfaces. Multiple scans may be conducted and the software may stitch the scans or maps together to form a larger map or maps using the positional information and if desired, anatomical locations or unique anatomical features, as well as other techniques. This enables a greater region to be displayed and also provide a greater region on which to plan and ablate Tissue 50. Additional imaging modality inputs and maps such as CT and MRI, as well as electrical inputs and maps (e.g. EKG) may be merged, integrated, registered and the like with the above Displays 30 and display properties.

Figure 9:
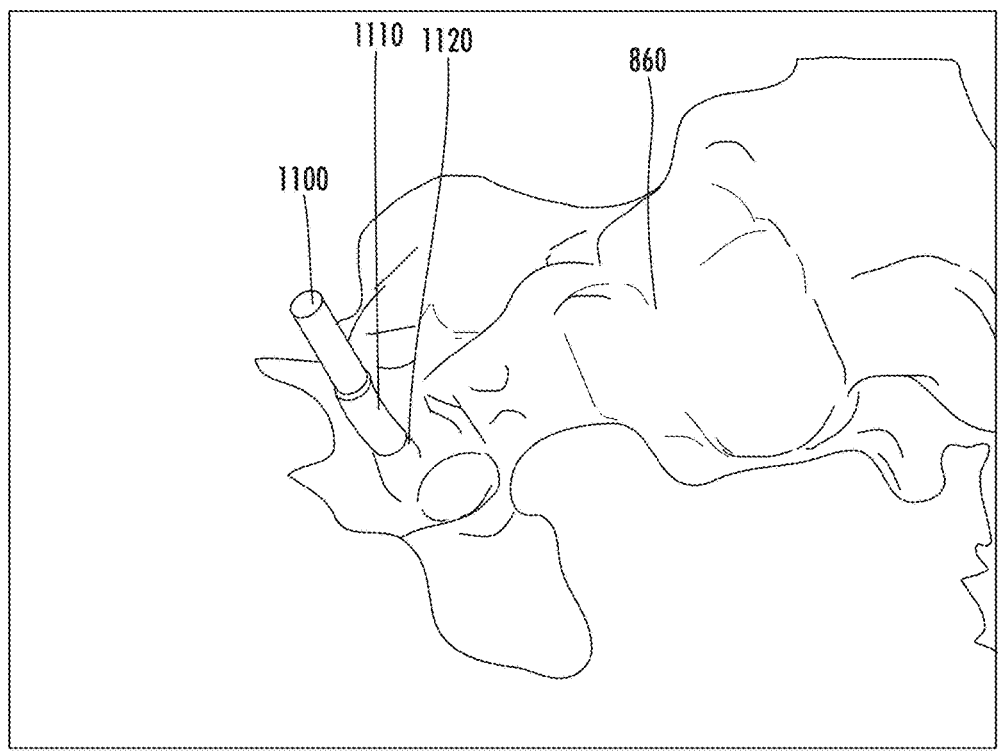
FIG. 9 illustrates an embodiment of a 3D map.

FIG. 9 is a 3D software generated image of the distance from the energy source to the Endocardium 950 from the ultrasound data depicting a portion of a left atrium, with color used for distance, including in-therapy range and out-of-therapy range, as well as a portion of the Catheter 120, including a Catheter Distal Tip Image 1120, an Inner Shaft Deflecting Section Image 1110, and a part of the Inner Shaft 220 proximal to the Inner Shaft Deflecting Section 230—Catheter Image 1100. A Display 30 of this type may be used as part of the Graphical User Interface of the present embodiments, typically as part of the initial mapping of a region of Tissue 50. 3D maps may be spatially correlated with 2D maps (e.g. M-mode as shown in FIGS. 8A-8C) and one-dimensional A-mode. These may be correlated with a pointing vector at the Catheter Distal Tip 240 in a Display 30.

Figure 10:
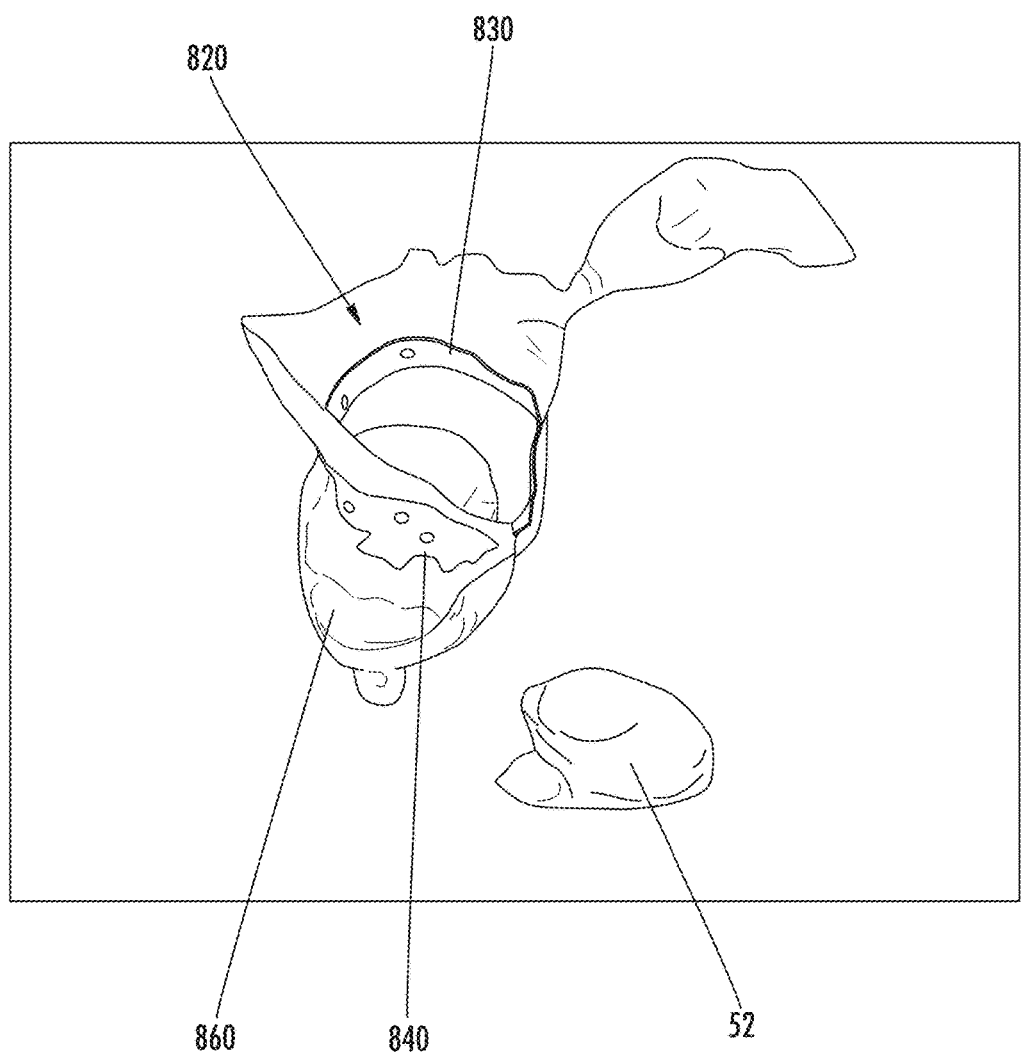
FIG. 10 illustrates an embodiment of a 3D map with a planned target lesion.

The System 10 provides the user the ability to cycle through various images and display a multitude of properties as discussed above. With that, the System 10 has provided the user with sufficient information to plan a Lesion 53. The user interacts with the graphical user interfaces and control inputs to draw an ablation line or lines, zone, and or region to be ablated. This may be done by placing the cursor on a section of the displayed image and clicking to start a Lesion 53 line, then moving the cursor to a new position and clicking again to make a Lesion Segment 830 (FIG. 10). This process may be continued until the entire Lesion Segment 830 is formed, including a Lesion Overlap 840. Double clicking the Mouse 32 may terminate the Lesion 53. Included in the Lesion 53 may be a selected depth or depths for the Lesion 53 to extend. In the Display 30, error bars (such as line width or region) may be displayed to indicate uncertainty. The area of uncertainty may be displayed as being different from the Planned Lesion 820. Examples of displaying the area of uncertainty may be by using a different line or region width, color, texture, haziness, transparency, etc. for the uncertainty, or simply by making the Lesion 53 show the minimum and or maximum area to be ablated, or any combination thereof.

Once the user draws the Planned Lesion 820, the System 10 software may calculate all the ablation parameters to form the Lesion 53. This may include but is not limited to energy density delivered, speed of the Energy Beam 290 along the Tissue 50, motion and angularity compensation, distance of the energy source from the Lesion 53 and Collateral Tissue 52, wall thickness or Tissue Thickness 51, Tissue 50 properties, etc. These parameters may be at least in part determined from a look up table. This information may be displayed to the user as well as baseline ablation parameters. In FIG. 5 a prescribed Dosing Plan 560 can correspond with lesion segments in the 3D Image 510. In some embodiments, a Graphical User Interface may include highlighted lesion segments on the 3D anatomical reference map image; a lesion path with distance from the energy source to the endocardium and epicardium, and the maximum therapy distance.

The user has the ability to tag or demarcate certain structures of interest (e.g. esophagus) in any of the maps and have those tags reflected in other maps. For example, tagging the esophagus in the maps shown in FIGS. 8A-8C would show up on the map shown in FIG. 3. Maps may also be tagged and cycled through with respect to cardiac and respiratory phases, which may be derived from the EM sensors with or without the use of an electrocardiogram.

The user may then modify the Planned Lesion 820 based on information obtained about the Lesion 53, Collateral Tissue 52, ablation parameters, etc. through the graphical user interfaces as described above. The user has the ability to move, manipulate, and change parameters on, along, and/or within the planned lesion by, for example, selecting a lesion segment with the Mouse 32, and dragging the lesion segment to a new position. This may include moving the entire Lesion 53, or point-to-point line segments, such as adding and or deleting points along the segment, or moving points or groups of points. The depth of the Lesion 53 may be adjusted as part of determining the Lesion 53, as well as energy delivery, etc. as previously discussed. One or more lesion segments may be selected either in the dosing plan or on the 3D anatomical reference map mage. The System 10 software may calculate the optimum position for the catheter to be located and pointed for the angle of incidence, distances with shortest ablation times, appropriate cross-over of the Lesion 53 ends, etc. The software may then provide on the graphical user interface a recommended position of the Catheter 120/Energy Beam 290 relative to the lesion path, indicating position by, for example, a line, a Catheter Image 1100, a shaded area, and the like. The user simply moves the Catheter 120/energy source/Energy Beam 290 to line up with an image on the display showing optimal positioning. During movement of the Catheter 120, the positional information, including that from EM sensors, enables the software to calculate and display the real-time motion of the Catheter 120/energy source/Energy Beam 290 on the Display 30 as well as update distances, etc.

FIG. 10 is an example of a 3D software generated image of the distance from the energy source to the Endocardium 950 from the ultrasound data depicting a portion of a left atrium with grayscale or color used for distance, including in-therapy range and out-of-therapy range and Collateral Tissue 52. In addition, shown is a Planned Lesion 820 line with Lesion Segments 830 along the line separated by the black dots, the Lesion Overlap 840, with the width of the Lesion 53 line representing the spatial uncertainty calculated by software based on a variety of inputs, such as EM senor position error, Catheter 120 tip position error, wall motion, etc.

Upon planning the Lesion 53, the user may desire to run a pre-therapy scan to confirm any or all aspects of the desired Lesion 53 only, or a smaller portion of Tissue 50 than in a larger map, prior to starting ablation. Using the graphical user interfaces of the present disclosure and control inputs, the user initiates the System 10 command to have the Catheter 120 automatically traverse a portion of or the entire Planned Lesion 820, or a portion of Tissue 50, and display any or all of the above listed parameters, such as the Catheter 120, energy source, and or energy/ultrasound beam position; display the ablation line, zone, depth, width, including error bars to indication uncertainty; display thickness of the target and Collateral Tissue 52 along/within the lesion path; display ablation parameters at any point or region on, along, or within the Planned Lesion 820; display regions of desirable and or undesirable motion; display regions of desirable and or undesirable angularity of the Catheter 120/energy source/Energy Beam 290; display regions of desirable and or undesirable distance; etc.

If a pre-therapy scan is run, the user has the ability to modify any aspect of the Planned Lesion 820 (baseline or modified), including repositioning the Catheter 120, and re-planning the Lesion 53. The user also has the ability to confirm the using the Graphical User Interfaces of the present embodiments.

Once the Lesion 53 is confirmed, the user, using the Graphical User Interface and control inputs, initiates the System 10 command to have the System 10 automatically execute the ablation. Irrigation flow may be automatically or manually modified throughout according to the monitored temperatures or to a preset value or values. The software commands the drive mechanisms in the Pod 110, or directly in the handle or Controller 20, to deflect the Inner Shaft Deflecting Section 230 to steer the Catheter Distal Tip 240 and Energy Beam 290 in a specific pattern while delivering the appropriate amount of energy, based on the varying parameters previously discussed, to complete the ablation.

During ablation, real-time information about all the System 10 operating parameters, Catheter 120 and ancillary device position, motion/angularity, ablation time, time to complete the ablation, temperatures (from the Catheter 120 and ancillary devices), irrigation flow, Tissue Thickness 51 at beam, Tissue Thickness 51 with respect to Collateral Tissue 52 and gap distance (gap between the catheter tip and tissue surface), Lesion 53 depth, Lesion 53 depth with respect to Tissue Thickness 51, distance to Collateral Tissue 52, Lesion 53 depth with respect to Collateral Tissue 52, depth of Lesion 53, Lesion 53 transmurality, etc.

The user has the ability at any time to pause or completely stop Catheter 120 motion, energy delivery, etc. by using the Graphical User Interface or for a complete stop, one of the emergency stop buttons, which may be located, for example, on the Catheter Handle 130, Pod 110, Controller 20 chassis, Touchscreen 33, etc.

Upon completion of the Lesion 53, the user can review all the parameters of the Lesion 53. The user can also order a post-ablation scan to characterize the Lesion 53 based on Tissue 50 properties. The System 10 may evaluate, for example, Tissue 50 elasticity through a repetitive push then listen mapping mode using radiation force for the pushes. The System 10 software may display areas of concern with questionable Lesion 53 formation. The System 10 may also be commanded to re-scan and re-plot a new Planned Lesion 820 to ensure full ablation of the Planned Lesion 820. Repeat ablation can be conducted using this or following the already described procedure workflow.

The Lesion 53 may be interrogated using an ancillary device (e.g. a lasso type catheter) or the Catheter 120 itself (e.g. with electrode on tip/distal region). Repeat ablation can be conducted using this or following the already described procedure workflow.

Additional ablations and interrogations can be conducted using the described workflow, such as for targeting other regions of Tissue 50, e.g. or cardiac lesions include pulmonary veins or vein pairs, roof line, isthmus line, ventricular tissue, renal arteries, ganglionated plexi, carotid bodies, etc.

Software may be included in the system described above to control any or all of the process described above, or the software may be run remotely and may be in communication with the local system to control the process. Thus, a computer implemented ablation System 10 may include software in a memory element that is used by a processor or controller to control any aspect of the system or methods described above.

While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only, and is not intended to limit the invention.

What is claimed is:

1. A user interface system for an ablation procedure, the system comprising:
   a display;
   a controller in electronic communication with the display;
   a catheter coupled to the controller, the catheter having a distal tip comprising an ultrasound transducer, wherein the ultrasound transducer is configured to emit an ultrasound beam; and
   a graphical user interface generated by the controller and shown on the display, wherein the graphical user interface comprises:
      a three-dimensional anatomical reference map of body tissue to be ablated, wherein a lesion path is superimposed on the anatomical reference map;
      a catheter position relative to the body tissue; and
      a window showing data, the data based on ultrasound information collected by the ultrasound transducer and including a distance between the ultrasound transducer and a surface of the body tissue, the distance displayed as a two-dimensional graph along a sensing pattern traversed by the ultrasound beam of the catheter.

2. The system of claim 1, wherein the data further comprises a dosing plan displayed as a two-dimensional graph along the lesion path.

3. The system of claim 1, wherein the data further comprises a tissue thickness displayed as a two-dimensional graph along the sensing pattern traversed by the ultrasound beam of the catheter.

4. The system of claim 1, wherein the graphical user interface displays ablation parameters along any portion of the lesion path.

5. The system of claim 1, wherein:
   the catheter comprises a plurality of electromagnetic sensors; and
   the graphical user interface further comprises a displayed combined characteristic, the combined characteristic based on combining the ultrasound information from the ultrasound transducer with position information from the plurality of electromagnetic sensors, wherein the ultrasound information comprises at least one of: an angle of incidence, an effective tissue thickness, a tissue property, and the distance between the ultrasound transducer and the surface of the body tissue.

6. The system of claim 1, wherein the catheter position or the data in the window are shown in real-time.

7. The system of claim 1, wherein the catheter position or the data in the window are shown as a static image synthesized over one or more phases of a cardiac cycle.

8. The system of claim 1, wherein the graphical user interface comprises a tool that allows a user to plan the lesion path using a selection option chosen from the group consisting of: free-form drawing, segmented drawing, choosing from a stored catalog of lesion paths, and modifying a displayed lesion path.

9. The system of claim 8, wherein the controller recommends the catheter position relative to the lesion path.

10. The system of claim 1, wherein the graphical user interface includes a spatial uncertainty of the lesion path or a lesion zone.

11. The system of claim 1, wherein the data further comprises a tissue property, and wherein the tissue property is one of compressibility, density, and stiffness.

12. A user interface system for an ablation procedure, the system comprising:
   a display;
   a controller in electronic communication with the display;
   a catheter coupled to the controller, the catheter having a distal tip comprising an ultrasound transducer, wherein the ultrasound transducer is configured to emit an ultrasound beam; and
   a graphical user interface generated by the controller and shown on the display, wherein the graphical user interface comprises:
      a three-dimensional anatomical reference map of body tissue to be ablated, wherein a lesion path is superimposed on the anatomical reference map;
      a catheter position relative to the body tissue; and
      a window showing data, the data based on ultrasound information collected by the ultrasound transducer and including at least one of a) a distance between the ultrasound transducer and a surface of the body tissue and b) a tissue thickness; and
   wherein the anatomical reference map is generated from the ultrasound information collected in an amplitude mode along a sensing pattern traversed by the ultrasound beam of the catheter.

13. The system of claim 12, wherein the distal tip of the catheter is moved by the controller to ablate the body tissue along the lesion path.

14. The system of claim 12, wherein the anatomical reference map displays a color map of an ablation range of the catheter, the ablation range including an in-therapy range and an out-of-therapy range.

15. A method for providing a user interface for an ablation procedure, the method comprising:
provided a user interface system comprising:
a display;
a controller in electronic communication with the display; and
a catheter coupled to the controller, the catheter having a distal tip comprising an ultrasound transducer, wherein the ultrasound transducer is configured to emit an ultrasound beam; and
generating, by the controller, a graphical user interface shown on the display, wherein the graphical user interface comprises:
a three-dimensional anatomical reference map of body tissue to be ablated, wherein a lesion path is superimposed on the anatomical reference map;
a catheter position relative to the body tissue; and
a window showing data, the data based on ultrasound information collected by the ultrasound transducer and including a distance between the ultrasound transducer and a surface of the body tissue, the distance displayed as a two-dimensional graph along a sensing pattern traversed by the ultrasound beam of the catheter.

16. The method of claim 15, wherein the data further comprises a dosing plan displayed as a two-dimensional graph along the lesion path.

17. The method of claim 15, wherein the data further comprises a tissue thickness displayed as a two-dimensional graph along the sensing pattern traversed by the ultrasound beam of the catheter.

18. The method of claim 15, wherein the anatomical reference map is generated from the ultrasound information collected in amplitude mode along the sensing pattern traversed by the ultrasound beam of the catheter.

19. The method of claim 15, further comprising displaying the anatomical reference map as a color map of an ablation range of the catheter, the ablation range including an in-therapy range and an out-of-therapy range.

20. The method of claim 15, wherein:
the catheter comprises a plurality of electromagnetic sensors; and
the method further comprises displaying a combined characteristic, the combined characteristic based on combining the ultrasound information from the ultrasound transducer with position information from the plurality of electromagnetic sensors, wherein the ultrasound information comprises at least one of: an angle of incidence, an effective tissue thickness, a tissue property, and the distance between the ultrasound transducer and the surface of the body tissue.

21. The method of claim 15, wherein the generating of the graphical user interface comprises displaying the catheter position or the data in the window in real-time.

22. The method of claim 15, wherein the data further comprises a tissue property, and wherein the tissue property is one of compressibility, density, and stiffness.

* * * * *